United States Patent
Burnett et al.

(10) Patent No.: US 11,034,722 B2
(45) Date of Patent: Jun. 15, 2021

(54) METHODS FOR EXTRACTING KERATIN PROTEINS

(71) Applicant: Keranetics, Inc., Winston-Salem, NC (US)

(72) Inventors: Luke Burnett, Winston-Salem, NC (US); Sarah Ann Boyd, Mooresville, NC (US)

(73) Assignee: Keranetics, Inc., Winston-Salem, NC (US)

(*) Notice: Subject to any disclaimer, the term of this patent is extended or adjusted under 35 U.S.C. 154(b) by 0 days.

(21) Appl. No.: 16/507,181

(22) Filed: Jul. 10, 2019

(65) Prior Publication Data

US 2019/0359650 A1   Nov. 28, 2019

Related U.S. Application Data

(62) Division of application No. 14/238,648, filed as application No. PCT/US2012/051192 on Aug. 16, 2012, now Pat. No. 10,385,095.

(60) Provisional application No. 61/524,541, filed on Aug. 17, 2011.

(51) Int. Cl.
*C07K 1/36* (2006.01)
*C07K 14/47* (2006.01)

(52) U.S. Cl.
CPC ............ *C07K 1/36* (2013.01); *C07K 14/4741* (2013.01)

(58) Field of Classification Search
None
See application file for complete search history.

(56) References Cited

U.S. PATENT DOCUMENTS

| | | |
|---|---|---|
| 2,993,794 A | 7/1961 | Moshy |
| 3,464,825 A | 9/1969 | Anker |
| 4,570,629 A | 2/1986 | Widra |
| 5,006,467 A | 4/1991 | Kusano et al. |
| 5,047,249 A | 9/1991 | Rothman et al. |
| 5,100,783 A | 3/1992 | Dean, Jr. et al. |
| 5,153,132 A | 10/1992 | Goodwin et al. |
| 5,300,285 A | 4/1994 | Halloran et al. |
| 5,320,796 A | 6/1994 | Harashima et al. |
| 5,358,935 A | 10/1994 | Smith et al. |
| 5,512,474 A | 4/1996 | Clapper et al. |
| 5,636,643 A | 6/1997 | Argenta et al. |
| 5,645,081 A | 7/1997 | Argenta et al. |
| 5,651,960 A | 7/1997 | Chan et al. |
| 5,651,966 A | 7/1997 | Read et al. |
| 5,679,819 A | 10/1997 | Jones et al. |
| 5,707,972 A | 1/1998 | Shimizu |
| 5,763,583 A | 6/1998 | Arai et al. |
| 5,852,024 A | 12/1998 | Pines et al. |
| 5,883,078 A | 3/1999 | Seelich et al. |
| 5,902,608 A | 5/1999 | Read et al. |
| 5,932,552 A | 8/1999 | Blanchard et al. |
| 5,948,432 A | 9/1999 | Timmons et al. |
| 5,972,335 A | 10/1999 | Ferguson et al. |
| 6,110,487 A | 8/2000 | Timmons et al. |
| 6,124,265 A | 9/2000 | Timmons et al. |
| 6,159,495 A | 12/2000 | Timmons et al. |
| 6,159,496 A | 12/2000 | Blanchard et al. |
| 6,165,496 A | 12/2000 | Timmons et al. |
| 6,251,379 B1 | 6/2001 | Omura et al. |
| 6,268,454 B1 | 7/2001 | Song et al. |
| 6,270,791 B1 | 8/2001 | Van Dyke et al. |
| 6,270,793 B1 | 8/2001 | Van Dyke et al. |
| 6,274,155 B1 | 8/2001 | Van Dyke et al. |
| 6,274,163 B1 | 8/2001 | Blanchard et al. |
| 6,316,598 B1 | 11/2001 | Van Dyke et al. |
| 6,371,984 B1 | 4/2002 | Van Dyke et al. |
| 6,379,690 B2 | 4/2002 | Blanchard et al. |
| 6,432,435 B1 | 8/2002 | Timmons et al. |
| 6,461,628 B1 | 10/2002 | Blanchard et al. |
| 6,544,548 B1 | 4/2003 | Siller-Jackson et al. |
| 6,634,945 B2 | 10/2003 | Glavich et al. |
| 6,696,073 B2 | 2/2004 | Boyce et al. |
| 6,746,836 B1 | 6/2004 | Widra |
| 6,783,546 B2 | 8/2004 | Zucherman et al. |
| 6,808,927 B2 | 10/2004 | Greenfield et al. |
| 6,825,323 B2 | 11/2004 | Hess |
| 6,833,488 B2 | 12/2004 | Bucevschi et al. |
| 6,858,383 B2 | 2/2005 | Sabbadini |
| 6,869,445 B1 | 3/2005 | Johnson |
| 7,148,327 B2 | 12/2006 | Kelly et al. |
| 7,439,012 B2 | 10/2008 | Van Dyke |

(Continued)

FOREIGN PATENT DOCUMENTS

| | | |
|---|---|---|
| CN | 102120753 | 7/2011 |
| GB | 351600 | 7/1931 |

(Continued)

OTHER PUBLICATIONS

Sorvall Evolution RC product information sheet (Thermo Scientific). Retrieved from < https://www.thermofisher.com/content/dam/tfs/LPG/LED/LED%20Documents/Product%20Manuals%20&%20Specifications/Centrifuges/Benchtop%20Centrifuges/Gene-ral%20Purpose%20Centirfuges/D17331.about..pdf> on Aug. 23, 2016.
Sierpinski et al., "The use of keratin biomaterials derived from human hair for the promotion of rapid regeneration of peripheral nerves", Biomaterials 29 (2008) 118-128.
ThermoFisher Scientific Press Release, May 8, 2006—Merger of Thermo Electron and Fisher Scientific. Retrieved from < http://ir.thermfisher.com/investors/news-and-events/news-releases/news-release-details/2006/Thermo-Electron-and-Fisher-Scientific-to-Combine-in-In-dustry-Transforming-Transaction/default.aspx? > on Aug. 24, 2016.

(Continued)

*Primary Examiner* — Suzanne M Noakes
(74) *Attorney, Agent, or Firm* — Massey Law, PLLC; Carl Massey

(57) ABSTRACT

Described herein are methods to produce keratin protein-based biomaterials, the parameters required to achieve improved extraction, the parameters required to improve isolation, the parameters of lyophilization and the grinding process to achieve consistent particulate sizes of protein materials.

12 Claims, 5 Drawing Sheets

(56) References Cited

U.S. PATENT DOCUMENTS

Figure 1:
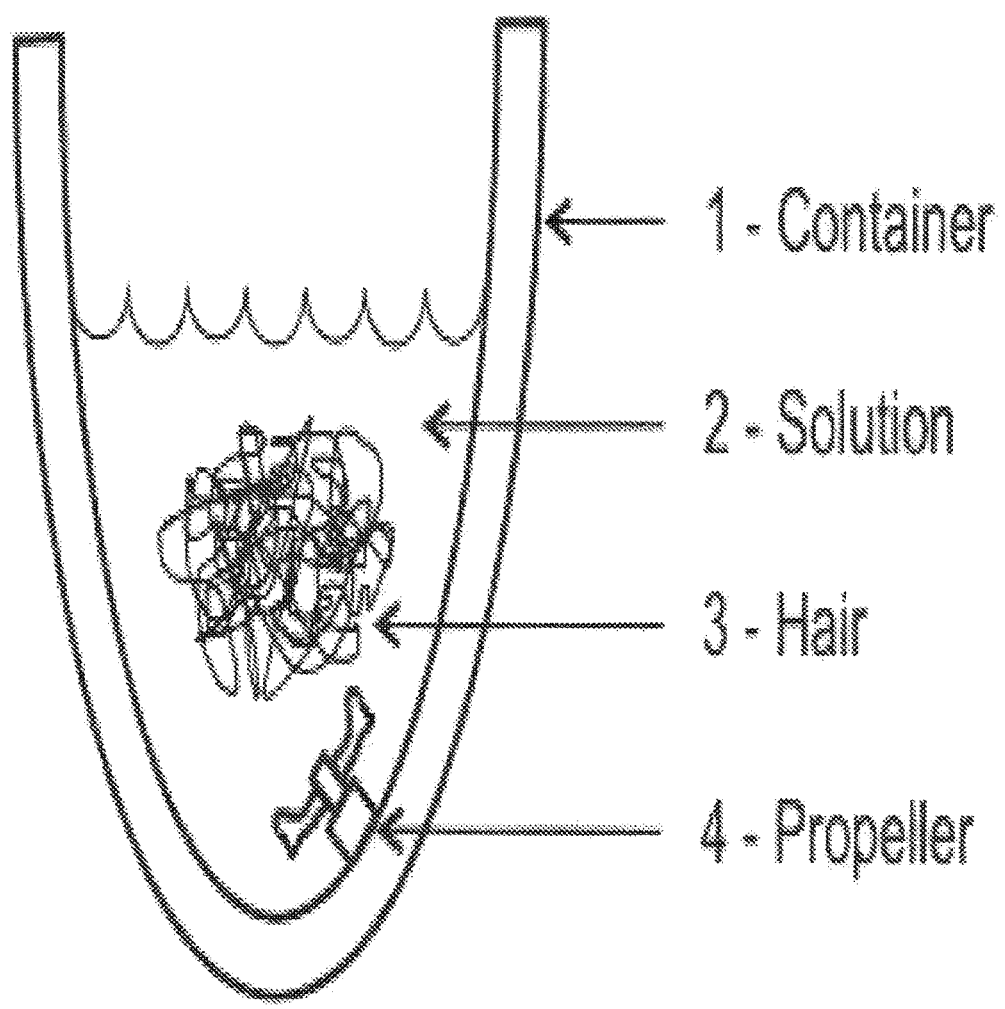

| | | | |
|---|---|---|---|
| 7,892,572 B2 | 2/2011 | Peplow et al. | |
| 7,892,573 B2 | 2/2011 | Van Dyke | |
| 8,021,830 B2 | 9/2011 | Van Dyke | |
| 8,258,093 B2 | 9/2012 | Van Dyke | |
| 8,273,702 B2 | 9/2012 | Van Dyke | |
| 8,299,013 B2 | 10/2012 | Van Dyke | |
| 9,700,631 B2 | 7/2017 | Burnett et al. | |
| 9,827,245 B2 | 11/2017 | Tomblyn et al. | |
| 2001/0021389 A1 | 9/2001 | Starling et al. | |
| 2001/0047082 A1 | 11/2001 | Van Dyke et al. | |
| 2002/0192196 A1 | 12/2002 | Allen-Hoffmann | |
| 2003/0049266 A1 | 3/2003 | Fearon et al. | |
| 2003/0109587 A1 | 6/2003 | Mori | |
| 2003/0204037 A1 | 10/2003 | Van Dyke | |
| 2003/0228353 A1 | 12/2003 | Cowsar | |
| 2004/0062793 A1 | 4/2004 | Van Dyke | |
| 2004/0076599 A1 | 4/2004 | Siller-Jackson et al. | |
| 2004/0078090 A1 | 4/2004 | Binette et al. | |
| 2004/0120910 A1 | 6/2004 | Van Dyke | |
| 2004/0267362 A1 | 12/2004 | Hwang et al. | |
| 2005/0058686 A1 | 3/2005 | Van Dyke | |
| 2005/0084542 A1 | 4/2005 | Rosenberg et al. | |
| 2005/0169963 A1 | 8/2005 | Van Dyke et al. | |
| 2006/0051732 A1 | 3/2006 | Van Dyke | |
| 2006/0140889 A1 | 6/2006 | Houtzager | |
| 2007/0166348 A1 | 7/2007 | Van Dyke | |
| 2007/0207111 A1 | 9/2007 | Nomura | |
| 2007/0208134 A1 | 9/2007 | Hunter et al. | |
| 2007/0298070 A1 | 12/2007 | Van Dyke | |
| 2008/0003676 A1 | 1/2008 | Sheridan et al. | |
| 2008/0038327 A1 | 2/2008 | Kelly et al. | |
| 2008/0274165 A1 | 11/2008 | Van Dyke | |
| 2009/0004242 A1 | 1/2009 | Van Dyke | |
| 2009/0017001 A1 | 1/2009 | Van Dyke | |
| 2009/0017031 A1 | 1/2009 | Fung | |
| 2009/0047260 A1 | 2/2009 | Van Dyke | |
| 2009/0209738 A1 | 8/2009 | Cranston | |
| 2010/0197021 A1 | 8/2010 | Van Dyke | |
| 2011/0137329 A1 | 6/2011 | Van Dyke | |
| 2011/0142910 A1 | 6/2011 | Van Dyke | |
| 2011/0217285 A1 | 9/2011 | Van Dyke et al. | |
| 2011/0217356 A1 | 9/2011 | Van Dyke et al. | |
| 2011/0300193 A1 | 12/2011 | Van Dyke | |
| 2012/0219667 A1 | 8/2012 | Kelly et al. | |
| 2012/0276188 A1 | 11/2012 | Barrows | |
| 2016/0324750 A1 | 11/2016 | Burnett et al. | |
| 2017/0281783 A1 | 10/2017 | Burnett et al. | |

FOREIGN PATENT DOCUMENTS

| | | |
|---|---|---|
| WO | 99/26570 | 6/1999 |
| WO | 99/26595 | 6/1999 |
| WO | 99/51175 | 10/1999 |
| WO | 00/76437 | 12/2000 |
| WO | 01/19283 | 3/2001 |
| WO | 01/19305 | 3/2001 |
| WO | 01/64033 | 9/2001 |
| WO | 02/45508 | 6/2002 |
| WO | 03/011894 | 2/2003 |
| WO | 03/064449 | 8/2003 |
| WO | 03/086491 | 10/2003 |
| WO | 2004/011052 | 2/2004 |
| WO | 2007/001339 | 1/2007 |
| WO | 2007/050387 | 5/2007 |
| WO | 2007/095151 | 8/2007 |
| WO | 2007/098053 | 8/2007 |
| WO | 2007/098114 | 8/2007 |
| WO | 2008/070091 | 6/2008 |
| WO | 2008/130607 | 10/2008 |
| WO | 2010/093882 | 10/2010 |
| WO | 2011/109808 | 9/2011 |
| WO | 2011/112575 | 9/2011 |
| WO | 2012/068376 | 5/2012 |
| WO | 2013/025928 | 2/2013 |
| WO | 2013/025940 | 2/2013 |
| WO | 2013/025941 | 2/2013 |
| WO | 2016/100476 | 6/2016 |

OTHER PUBLICATIONS

Nakamura et al., "A Rapid Extraction Procedure of Human Hair Proteins and Identification of Phosphorylated Species", Biol. Pharm. Bull. 25(5) 569-572 (2002).

Science gateway Centrifuge Rotor Speed Calculator Tool—Retrieved from < http://www.sciencegateway.org/tools/rotor.htm > on Aug. 23, 2016.

Barnstead/Lab-Line MAx Q 4000 Shaker Manual; Retrieved from < https://www.artisantg.com/info/ATGpajiz.pdf > on Sep. 6, 2017.

"Dialysis Methods for Protein Research", ThermoFisher Scientific, Retrieved from < https://www.thermofisher.com/us/en/home/life-science/protein-biology/prot-ein-biology-learning-center/protein-biology-resource-library/pierce-protei-n-methods/dialysis-methods-protein-research.html > on Sep. 7, 2017.

"Tangential How Filtration", PALL Laboratory, Retrieved from < https://laboratory.pall.com/en/tangential-flow-filtration.html > on Sep. 7, 2017.

Mechanical Mixing—Retrieved from San Diego Miramar Collage ChemPages Laboratory Resources < http://faculty.sdmiramar.edu/fgarces/labmatters/chemtech/modules/mixing/m-ixmech.htm > on Mar. 6, 2018.

Millipore Tangential How Filtration from 2003 < http://wolfson.huji.ac.il/purification/PDF/dialysis/MILLIPORE_TFF.pdf > downloaded Mar. 16, 2018.

De Guzman et al., Mechanical and biological properties of keratose biomaterials. Biomaterials. Nov. 2011;32 (32):8205-17.

Hill et al., Some properties of keratin biomaterials: kerateines. Biomaterials. Feb. 2010;31(4):585-93.

Peters et al., Observations upon a compound of mustard gas and kerateine. Biochem J. 1947;41(4):550-5.

Peyton et al., Halofuginone infused keratin hydrogel attenuates adhesions in a rodent cecal abrasion model. J Surg Res. Dec. 2012;178(2):545-52.

Saul et al., Keratin hydrogels support the sustained release of bioactive ciprofloxacin. J Biomed Mater Res A. Sep. 15, 2011;98(4):544-53.

METHODS FOR EXTRACTING KERATIN PROTEINS

CROSS-RELATION TO OTHER APPLICATIONS

This application is a division of U.S. patent application Ser. No. 14/238,648 filed Oct. 27, 2014, which is a national phase of International (PCT) Application No. PCT/US2012/051192, filed Aug. 16, 2012, claiming benefit of U.S. Provisional Patent Application No. 61/524,541, filed Aug. 17, 2011.

1. FIELD OF THE INVENTION

This invention relates to methods to extract and purify keratin protein-based biomaterials.

2. BACKGROUND OF THE INVENTION

Keratins are a family of proteins found in the hair, skin, and other tissues of vertebrates. Hair is a unique source of human keratins because it is one of the few human tissues that are readily available and inexpensive. Although other sources of keratins are acceptable feedstocks for the present invention (e.g. wool, fur, horns, hooves, beaks, feathers, scales, and the like), human hair is preferred because of its biocompatibility in human medical applications.

Keratins can be extracted from human hair fibers by oxidation or reduction using methods that have been widely published in the art. If one employs a reductive treatment, the resulting keratins are referred to as kerateines. If an oxidative treatment is used, the resulting keratins are referred to as keratoses. These methods typically employ a two-step process whereby the crosslinked structure of keratins is broken down by either oxidation or reduction. In these reactions, the disulfide bonds in cystine amino acid residues are cleaved, rendering the keratins soluble without appreciable disruption of amide bonds. Many of the keratins can remain trapped within the cuticle's protective structure, so a second-step using a denaturing solution is typically employed to effect efficient extraction of the cortical proteins (alternatively, in the case of oxidation reactions, these steps can be combined). This step has also been widely published in the art as solutions such as urea, transition metal hydroxides, surfactant solutions, and combinations thereof have been employed. Common methods include the use of aqueous solutions of tris(hydroxymethyl) aminomethane in concentrations between 0.1 and 1.0M, and urea solutions between 0.1 and 10M.

Many protein purification techniques are known in the art and range from the most simplistic such as fractional precipitation, to the most complex such as immunoaffinity chromatography. For example, sub-families of acidic and basic keratins have been described as being separable by moving bounding electrophoresis, but these fractions or their properties have not been described.

The methods that have been described in the art to extract these proteins rely on a chemical process of oxidation or reduction with less than optimal extraction. Accordingly, there is a great need to provide an optimized protein extraction procedure that provides a highly pure keratin protein product that retains structure and function.

3. SUMMARY OF THE INVENTION

Disclosed herein are methods to extract and purify keratin protein-based biomaterials. In some embodiments, the invention provides methods to produce keratin protein-based biomaterials, the parameters required to achieve improved extraction, the parameters required to improve isolation, the parameters of lyophilization and the grinding process to achieve consistent particulate sizes of protein materials.

The invention also provides methods to extract keratin proteins comprising: a) treating a keratin protein source with an oxidizing or reducing agent to solubilize keratin proteins; b) separating the soluble proteins from the keratin protein source by high speed centrifugation to produce a clarified soluble keratin protein solution; and c) lyophilizing the clarified soluble keratin protein solution into a keratin protein cake, wherein degradation of said keratin protein is minimized.

The invention also provides methods to extract keratin proteins comprising: a) treating a keratin protein source with an oxidizing or reducing agent to solubilize keratin proteins; b) separating the soluble proteins from the keratin protein source by high speed centrifugation to produce a clarified soluble keratin protein solution; and c) dialyzing the clarified soluble keratin protein solution wherein degradation of said keratin protein is minimized.

4. BRIEF DESCRIPTION OF THE FIGURES

Figure 2:
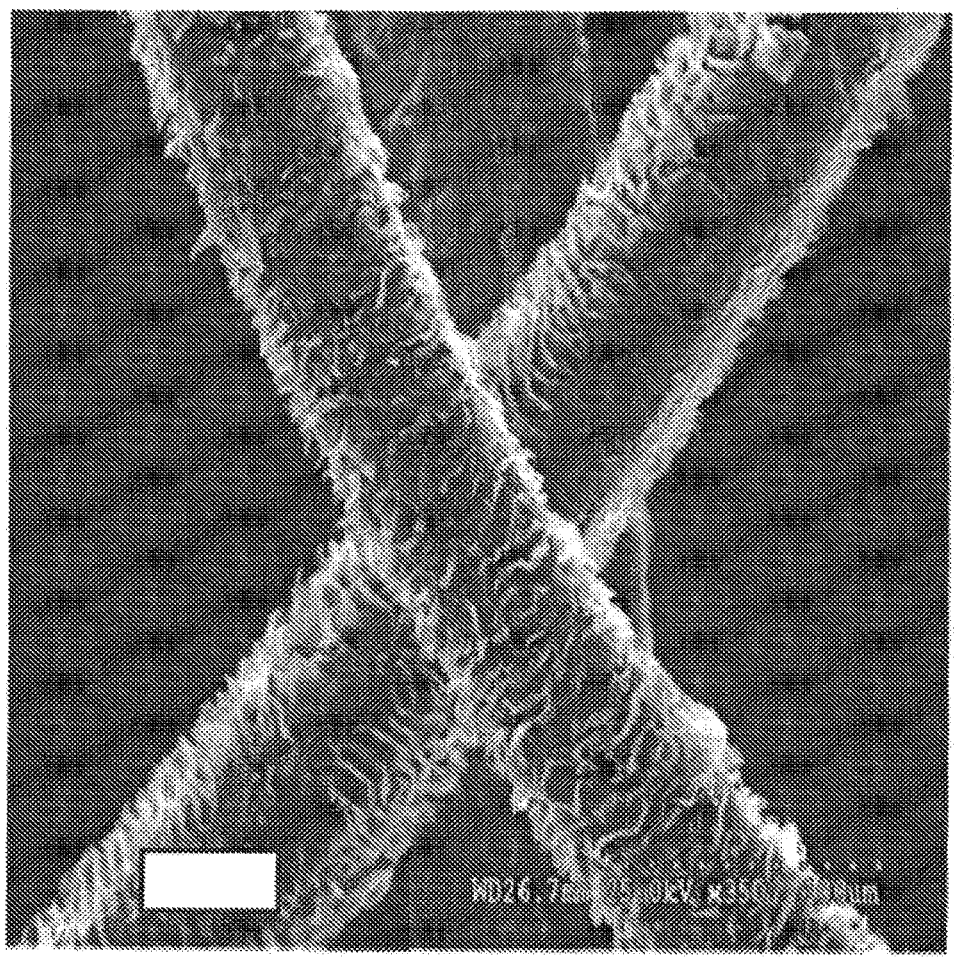

FIG. 1 depicts a cartoon showing a potential mixing container that provides mechanical agitation FIG. 2 is a scanning electron micrograph of hair shafts after 12 hours of mechanical mixing in the presence of an oxidant.

Figure 3A:
Figure 3B:
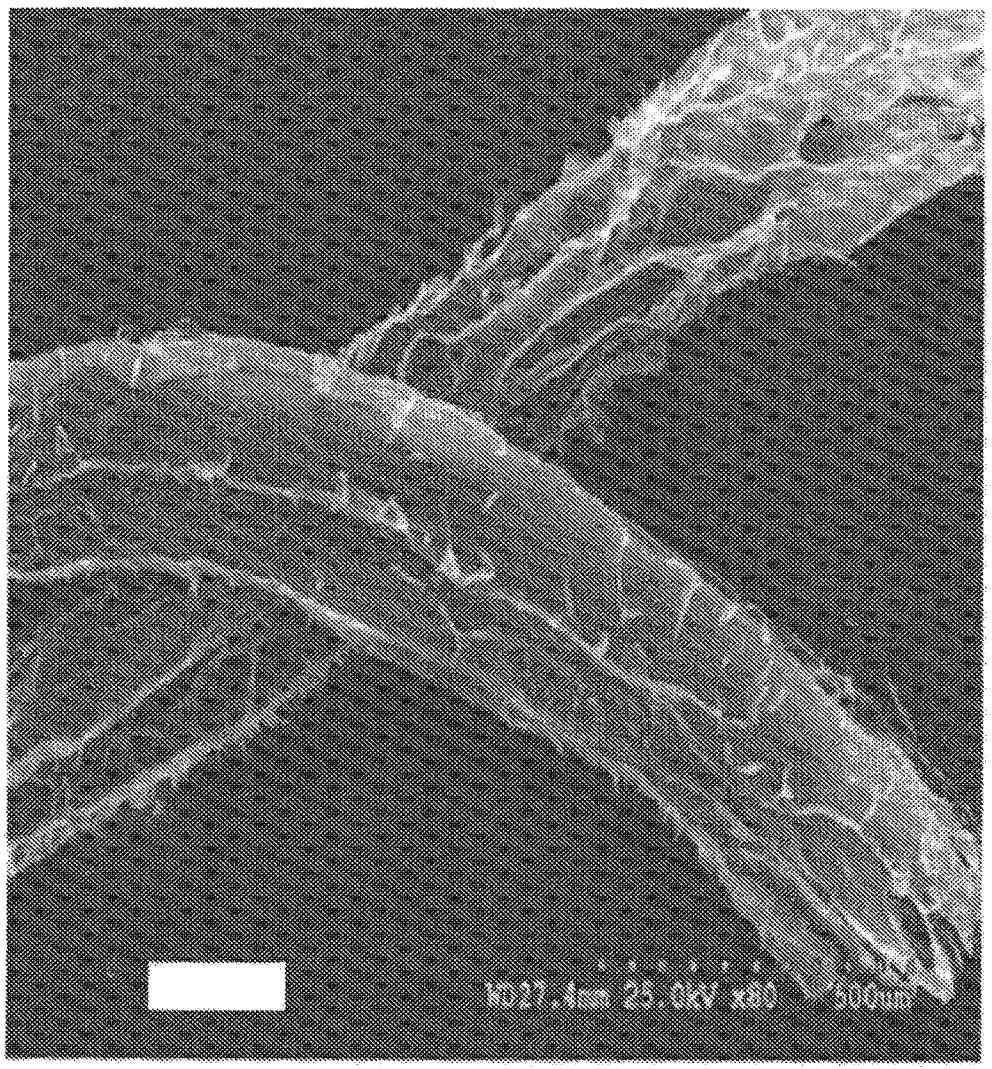

FIGS. 3A and 3B depict hair after base extraction. FIG. 3A is a picture of hair after base extraction. FIG. 3B is a scanning electron micrograph of a hair shaft after base extraction. The shaft is split in half and the majority of its cortical proteins (alpha and gamma keratins) have been removed during extraction, leaving the outer beta keratin hair covering.

Figure 4:
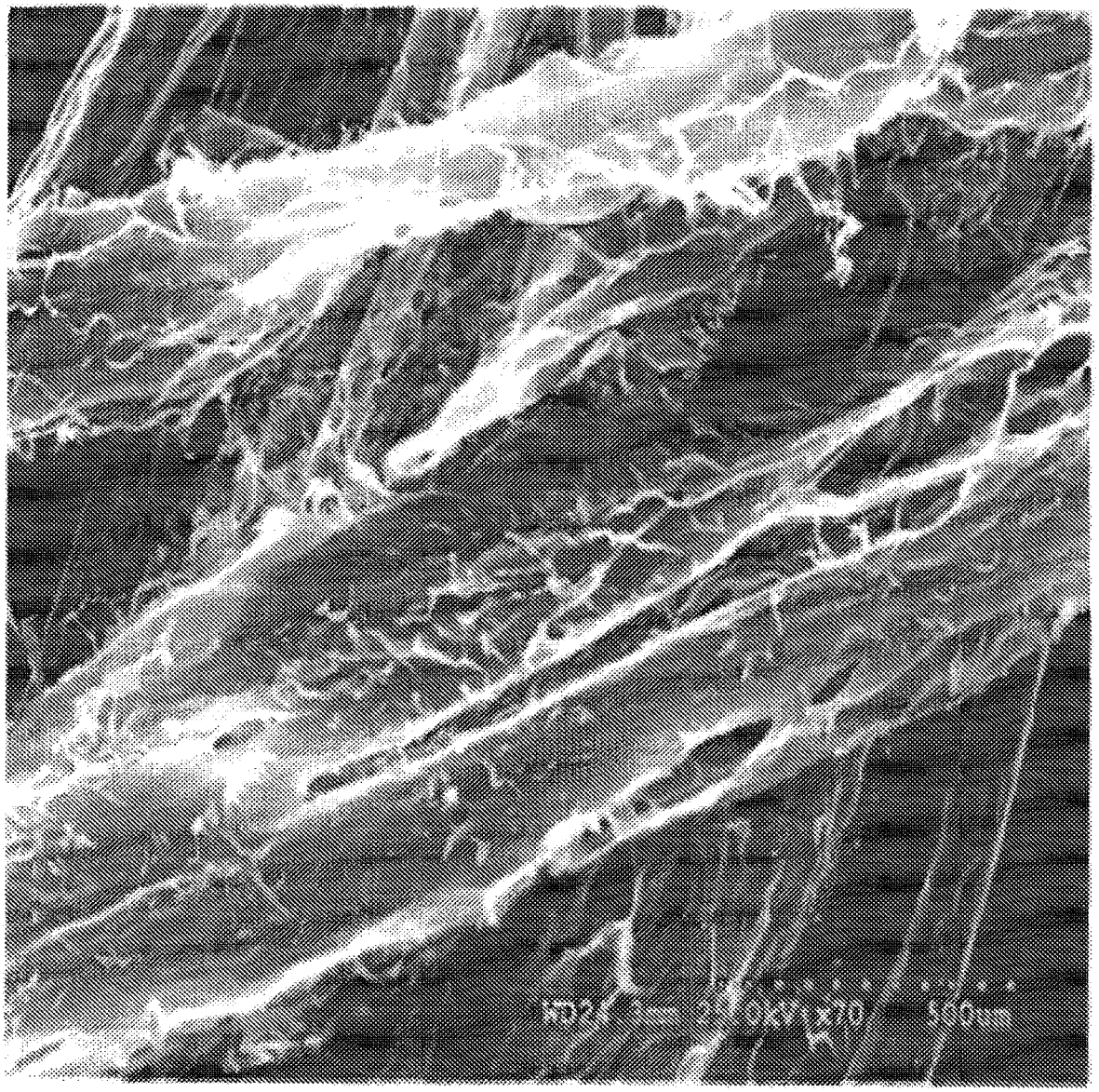

FIG. 4 is a scanning electron micrograph of hair shafts after final water extraction. The majority of cortical proteins are extracted and only the residual beta keratin hard coverings of the hair shafts appear to remain.

5. DETAILED DESCRIPTION

"Keratin protein source" as used herein includes proteinaceous sources of keratin proteins including but not limited human or animal wool, fur, horns, hooves, beaks, feathers, scales, and the like.

"Keratin protein(s)" as used herein collectively refers to keratin in keratin protein sources, including but not limited to naturally occurring keratin, reduced keratin, and/or oxidized keratin, or S-sulfonated keratin. This term also refers to the extracted keratin derivatives that are produced by oxidative and/or reductive treatment of keratin, including but not limited to keratose, alpha-keratose, gamma-keratose, kerateine, alpha-kerateine, or gamma-kerateine.

"Clarified keratin protein solution" as used herein refers to a solution comprising extracted keratin proteins that has undergone at least one high speed centrifugation step to clarify the solution of other contaminants.

"Keratin protein cake", "lyophilized protein cake", or "protein cake" as used herein includes but is not limited to a freeze-dried and/or vacuum dried keratin protein composition that exhibits long-term stability, short reconstitution time, uniform appearance, and low moisture content. Further, in some embodiments, "keratin protein cake", "lyophilized protein cake", or "protein cake" refers to compositions substantially free of bulking agents or stabilizers.

Keratin Protein Sources

Keratins are a family of proteins found in the hair, skin, and other tissues of vertebrates. Hair is a common source of human keratins because it is one of the few human tissues that is readily available and inexpensive. Other sources of keratins are acceptable feedstocks for the present invention, (e.g., wool, fur, horns, hooves, beaks, feathers, scales, and the like). Human hair is often used with human subjects because of its biocompatibility. Accordingly, in some embodiments, human hair is the keratin protein source The human hair can be end-cut, as one would typically find in a barber shop or salon.

Keratin Proteins

Soluble keratins can be extracted from human hair fibers by oxidation or reduction using methods known in the art. These methods typically employ a two-step process whereby the crosslinked structure of keratins is broken down by either oxidation or reduction. In these reactions, the disulfide bonds in cystine amino acid residues are cleaved, rendering the keratins soluble. The cuticle is essentially unaffected by this treatment, so the majority of the keratins remain trapped within the cuticle's protective structure. In order to extract these keratins, a second step using a denaturing solution is employed. Alternatively, in the case of reduction reactions, these steps can be combined. Denaturing solutions known in the art include urea, transition metal hydroxides, surfactant solutions, and combinations thereof. Common methods use aqueous solutions of tris base (2-Amino-2-(hydroxymethyl)-1,3-propanediol) in concentrations between 0.1 and 1.0 M, and urea solutions between 0.1 and 10M, for oxidation and reduction reactions, respectively.

If one employs an oxidative treatment, the resulting keratins are referred to as "keratoses." If a reductive treatment is used, the resulting keratins are referred to as "kerateines."

Crude (unfractionated) extracts of keratins, regardless of redox state, can be further refined into matrix (KAP and gamma), alpha, and/or charged (acidic or basic) fractions by a variety of methods such as isoelectric precipitation, dialysis, or high performance liquid chromatography (HPLC), as desired. In a crude extract, the alpha fraction begins to precipitate below pH 6 and is essentially completely precipitated by pH 4.2.

In some embodiments, KAP co-precipitate with the alpha fraction, thereby producing an alpha/KAP mixture.

High molecular weight keratins, or "alpha keratins," (alpha helical), are thought to originate from the microfibrillar regions of the hair follicle, and typically range in molecular weight from about 40-50 kiloDaltons for monomers and 80-100 kiloDaltons for dimers. Low molecular weight keratins, or "gamma keratins," or keratin-associated proteins (globular), are thought to originate from the matrix regions of the hair follicle, and typically range in molecular weight from about 3-30 kiloDaltons for KAP and 10-15 kiloDaltons for gamma keratins.

In some embodiments, the keratin preparations (particularly alpha and/or gamma kerateine and alpha and/or gamma-keratose) have an average molecular weight of from about 10 to about 70 or about 85 or about 100 kiloDaltons. Other keratin derivatives, particularly meta-keratins, may have higher average molecular weights, e.g., up to 200 or 300 kiloDaltons.

Even though alpha and gamma keratins possess unique properties, the properties of subfamilies of both alpha and gamma keratins can only be revealed through more sophisticated means of purification and separation such as provided herein. Additional properties that are beneficial emerge and can be optimized upon further separation and purification of crude keratin extracts.

Keratose Production

One method for the production of keratoses is by oxidation of keratin with hydrogen peroxide, peracetic acid, or performic acid. In a specific embodiment, the oxidant is peracetic acid. Generally, a solution of peracetic acid is used at a concentration range of about 1% to about 10%. A specific concentration used can be a 2% solution of peracetic acid. In some embodiments, the oxidant concentrations range from a ratio of about 5:1 to about 50:1 weight to weight to the keratin protein source to be extracted. A specific embodiment uses a weight to weight ratio of 25:1 of a 2% peracetic acid solution. In other embodiments, the weight to weight ratio is about 30:1 Those skilled in the art will recognize that slight modifications to the concentration can be made to affect varying ° of oxidation, with concomitant alterations in reaction time, temperature, and liquid to solid ratio. It has also been discussed that performic acid offers the advantage of minimal peptide bond cleavage compared to peracetic acid. However, peracetic acid offers the advantages of cost and availability. In some embodiments, the oxidation temperature is between 0 and 100° Celsius. In a specific embodiment, the oxidation temperature is 37° C. In some embodiments, the oxidation time is between 0.5 and 24 hours. In a specific embodiment, the oxidation time is 12 hours. In some embodiments, mechanical mixing is used to maximize oxidation efficiency. Additional yield can be achieved with subsequent extractions with dilute solutions of oxidant or water. After oxidation, the keratin protein source can be rinsed free of residual oxidant using copious amounts of purified water. In some embodiments, the oxidized keratin protein source is washed with water until residual oxidant is removed. In some embodiments, the washing step is performed until the washed keratin protein source does not test positive for oxidant. In a specific embodiment, the washed keratin protein source has about 5 ppm or less residual oxidant.

The keratoses may be extracted from the oxidized keratin protein source using an aqueous solution of a denaturing agent. Protein denaturants are well known in the art, including but not limited to, urea, transition metal hydroxides (e.g. sodium and potassium hydroxide), ammonium hydroxide, and tris(hydroxymethyl)aminomethane (Tris, also known as Trizma® base). In some embodiments, Tris is used at a ratio of about 5:1 to about 50:1 weight of protein source to a Tris solution of a concentration of about 0.01 to 1M. In other specific embodiments, the ratio is 25:1 or 40:1. In another specific embodiment, Tris is used at a concentration of 100 mM. Those skilled in the art will recognize that slight modifications to the concentration can be made to effect varying degree of extraction, with concomitant alterations in reaction time, temperature, and liquid to solid ratio. In some embodiments, the extraction temperature is between 0° and 100° Celsius. In a specific embodiment, the extraction temperature is 37° C. In some embodiments, the extraction time is between 0.5 and 24 hours. In a specific embodiment, the extraction time is about 2 hours. Additional yield can be achieved with subsequent extractions with dilute solutions of Tris or purified water. Often, the extraction is performed with mechanical agitation in a mixing tank to ensure a more efficient yield.

Kerateine Production

Similar to the methods described above for extraction and purification of keratoses, kerateines can be produced by reduction of a keratin protein source with thioglycolic acid or beta-mercaptoethanol. Specifically, thioglycolic acid (TGA) is often used. In some embodiments, TGA is added to the keratin protein source at a ratio of about 5:1 to about 50:1. In a specific embodiment, TGA is added at a ratio of 25:1. The TGA is added at a solution ranging in concentrations from about 0.1 to about 10M. In a specific embodiment, the TGA is added in solution at a concentration of 0.5M. During extraction, mechanical agitation is used to maximize extraction efficiency.

The solution containing reductant and extracted kerateine proteins (soluble keratin protein solution) is the collected and stored by straining the keratin protein source through a 400 micron mesh and storing the solution at 4° C. A base is then added to the drained keratin protein source in a ratio of about 10:1 to about 50:1. In a specific embodiment, the base is added to the drained keratin protein source at a ratio of 25:1. In some embodiments, the base is Tris generally used at a concentration of about 100 mM. The keratin protein source in the solution with base is mixed with agitation of about 2 hours at 37° C. The solution containing the base and extracted keratin proteins (soluble keratin protein solution) is then filtered and added to the first extracted solution and stored.

Those skilled in the art will recognize that slight modifications to the concentration can be made to effect reduction, with concomitant alterations in pH, reaction time, temperature, and liquid to solid ratio. In some embodiments, the reduction is performed at a temperature between 0 and 100° Celsius. In a specific embodiment, the temperature is 37° C. In some embodiments, the reduction time is between 0.5 and 24 hours. In a specific embodiment, the reduction is performed for 15 hours. Unlike the previously described oxidation reaction, reduction is carried out at basic pH. That being the case, keratins are highly soluble in the reduction media and are expected to be extracted. The reduction solution may therefore be combined with the subsequent extraction solutions and processed accordingly. The reduction is carried out with mechanical agitation in a mix tank to increase the efficiency of the reduction of the keratin proteins.

Residual reductant and denaturing agents can be removed from solution by dialysis. Typical dialysis conditions are 1 to 2% solution of kerateines dialyzed against purified water. Those skilled in the art will recognize that other methods exist for the removal of low molecular weight contaminants in addition to dialysis (e.g. microfiltration, chromatography, and the like). Once dissolved, the kerateines are stable in solution without the denaturing agent for finite periods. Therefore, the denaturing agent can be removed without the resultant precipitation of kerateines. Regardless of the fractionation/purification process, the resulting kerateines can be concentrated and lyophilized, similar to keratoses.

A soluble keratin protein solution is produced by the extraction of keratose and/or kerateine by either oxidative means for keratose, or by reductive means for kerateine.

In some embodiments, the soluble keratin protein solution may comprise 80%, 85%, 90%, 95%, 99% or more keratose. The keratose may be alpha-keratose or gamma-keratose, or some combination thereof. In some embodiments, the keratose in the soluble keratin protein solution comprises 50%, 55%, 60%, 65%, 70%, 75%, 80%, 85%, 90%, 95%, 99% or more alpha-keratose. In other embodiments, the keratose in the soluble keratin protein solution comprises 50%, 55%, 60%, 65%, 70%, 75%, 80%, 85%, 90%, 95%, 99% or more gamma-keratose.

In some embodiments, the soluble keratin protein solution may comprise 80%, 85%, 90%, 95%, 99% or more kerateine. The kerateine may be alpha-kerateine or gamma kerateine, or some combination thereof. In some embodiments, the kerateine in the soluble keratin protein solution comprises 50%, 55%, 60%, 65%, 70%, 75%, 80%, 85%, 90%, 95%, 99% or more alpha-kerateine. In other embodiments, the kerateine in the soluble keratin protein solution comprises 50%, 55%, 60%, 65%, 70%, 75%, 80%, 85%, 90%, 95%, 99% or more gamma-kerateine.

High Speed Centrifugation

In order to remove many of the keratin associated proteins and other proteins extracted through either oxidative or reductive processes listed above, a high speed centrifugation step is used. Current methods known in the art generally use a low speed centrifugation (around 4,000 rpm) to clear particulate matter. However, this speed does not create enough force to remove many of the protein contaminants present in the extracted protein solution. Thus, in some embodiments, high speed centrifugation is employed. Speeds in excess of about 5,000 rpm to about 30,000 rpm can be used. In a specific embodiment, the extracted protein solution is spun at about 20,000 rpm to produce a clarified protein solution. In another specific embodiment, the high speed centrifugation step is performed at about 4° C.

A clarified protein solution is produced by the high speed centrifugation of the soluble keratin protein solution.

In some embodiments, the clarified protein solution may comprise 80%, 85%, 90%, 95%, 99% or more keratose. The keratose may be alpha-keratose or gamma-keratose, or some combination thereof. In some embodiments, the keratose in the clarified protein solution comprises 50%, 55%, 60%, 65%, 70%, 75%, 80%, 85%, 90%, 95%, 99% or more alpha-keratose. In other embodiments, the keratose in the clarified protein solution comprises 50%, 55%, 60%, 65%, 70%, 75%, 80%, 85%, 90%, 95%, 99% or more gamma-keratose.

In some embodiments, the clarified protein solution may comprise 80%, 85%, 90%, 95%, 99% or more kerateine. The kerateine may be alpha-kerateine or gamma kerateine, or some combination thereof. In some embodiments, the kerateine in the clarified protein solution comprises 50%, 55%, 60%, 65%, 70%, 75%, 80%, 85%, 90%, 95%, 99% or more alpha-kerateine. In other embodiments, the kerateine in the clarified protein solution comprises 50%, 55%, 60%, 65%, 70%, 75%, 80%, 85%, 90%, 95%, 99% or more gamma-kerateine.

Dialysis

In many instances during protein purification, dialysis is used to separate or even to concentrate certain protein species present in the sample. Accordingly here, in many embodiments, the clarified protein solution is subjected to a dialysis step to fractionate certain protein species. In some embodiments, a 100 kDa molecular weight cutoff membrane is employed in the purification of alpha-keratose or alpha-kerateine. In other embodiments, a 5 kDa molecular weight cutoff membrane is employed to purify gamma-keratose or gamma kerateine. A common matrix for the dialysis membranes is regenerated cellulose, however, many other membrane preparations suitable for protein purification may be used.

In many instances, pressure is applied to aid in the dialysis process. If the pressure applied is too low, the resultant solutions contain greater protein fragments and peptides. Conversely, if the pressure is too high, the result is protein complex degradation. Thus, in some embodiments, the dialysis is performed under conditions that maintain a trans-membrane pressure from about 30 psi to about 40 psi (alpha) and about 50 psi to about 70 psi (gamma). Further, it is important to minimize the heat buildup developed by the shear stress of pressurized dialysis. Thus, in some embodiments, the dialysis is carried out at a temperature from about 4° C. to about 20° C. In a specific embodiment, the dialysis is carried out at about 15° C. to about 20° C.

Additionally, as the solution is dialyzed, the conductivity is adjusted. In some embodiments, the conductivity is adjusted down to about or below 0.6 mS. In some instances, the conductivity is adjusted with water.

Post dialysis, the clarified protein solution may comprise 80%, 85%, 90%, 95%, 99% or more keratose. The keratose may be alpha-keratose or gamma-keratose, or some combination thereof. In some embodiments, the keratose in the clarified protein solution post dialysis comprises 30%, 35%, 40%, 45%, 50%, 55%, 60%, 65%, 70%, 75%, 80%, 85%, 90%, 95%, 99% or more alpha-keratose. In other embodiments, the keratose in the clarified protein solution post dialysis comprises 30%, 35%, 40%, 45%, 50%, 55%, 60%, 65%, 70%, 75%, 80%, 85%, 90%, 95%, 99% or more gamma-keratose. In alternative embodiments, the clarified protein solution post dialysis is substantially free of alpha-keratose. In yet other alternative embodiment, the clarified protein solution post dialysis is substantially free of gamma-keratose.

Post dialysis, the clarified protein solution may comprise 80%, 85%, 90%, 95%, 99% or more kerateine. The kerateine may be alpha-kerateine or gamma-kerateine, or some combination thereof. In some embodiments, the kerateine in the clarified protein solution post dialysis comprises 30%, 35%, 40%, 45%, 50%, 55%, 60%, 65%, 70%, 75%, 80%, 85%, 90%, 95%, 99% or more alpha-kerateine. In other embodiments, the kerateine in the clarified protein solution post dialysis comprises 30%, 35%, 40%, 45%, 50%, 55%, 60%, 65%, 70%, 75%, 80%, 85%, 90%, 95%, 99% or more gamma-kerateine. In alternative embodiments, the clarified protein solution post dialysis is substantially free of alpha-kerateine. In yet other alternative embodiment, the clarified protein solution post dialysis is substantially free of gamma-kerateine.

Lyophilization

Storage of proteins for any length of time can pose stability problems. While working with proteins in the lab, they should be kept on ice. Since proteins are generally more stable at colder temperatures, maintenance at low temperatures even for short duration is recommended. Typically, proteins can be freeze-dried (lyophilized) to achieve storage conditions while maintaining protein stability.

In some embodiments, lyophilization is used to produce a protein cake of purified protein post-dialysis. The lyophilization is used to stabilize the extracted keratin proteins. Methods known in the art such as shell freezing followed by vacuum or bulk freezing and applying high heat tend to degrade proteins. Accordingly, in some embodiments, a keratin protein cake, comprising keratose and/or kerateine is produced by a lyophilization of a clarified keratin protein solution, optionally after dialysis.

In some embodiments, the clarified protein solution post-dialysis is bulk frozen at about −40° C., then a vacuum is applied until the containment containing the solution reaches about 250 torr. In some embodiments, heat is then applied in a step-wise fashion, bringing the material to about 0° C., then to about 25° C., then to about 37° C., while maintaining 250 torr pressure. In some embodiments, the lyophilization process occurs over a 24 hour period.

In some embodiments, the keratin protein cake may comprise 80%, 85%, 90%, 95%, 99% or more keratose. The keratose may be alpha-keratose or gamma-keratose, or some combination thereof. In some embodiments, the keratose in the keratin protein cake comprises 30%, 35%, 40%, 45%, 50%, 55%, 60%, 65%, 70%, 75%, 80%, 85%, 90%, 95%, 99% or more alpha-keratose. In other embodiments, the keratose in the keratin protein cake comprises 30%, 35%, 40%, 45%, 50%, 55%, 60%, 65%, 70%, 75%, 80%, 85%, 90%, 95%, 99% or more gamma-keratose. In alternative embodiments, the keratin protein cake is substantially free of alpha-keratose. In yet other alternative embodiments, the keratin protein cake is substantially free of gamma-keratose.

In some embodiments, the keratin protein cake may comprise 80%, 85%, 90%, 95%, 99% or more kerateine. The kerateine may be alpha-kerateine or gamma-kerateine, or some combination thereof. In some embodiments, the kerateine in the keratin protein cake comprises 30%, 35%, 40%, 45%, 50%, 55%, 60%, 65%, 70%, 75%, 80%, 85%, 90%, 95%, 99% or more alpha-kerateine. In other embodiments, the kerateine in the keratin protein cake comprises 30%, 35%, 40%, 45%, 50%, 55%, 60%, 65%, 70%, 75%, 80%, 85%, 90%, 95%, 99% or more gamma-kerateine. In alternative embodiments, the keratin protein cake is substantially free of alpha-kerateine. In yet other alternative embodiments, the keratin protein cake is substantially free of gamma-kerateine.

Grinding

Precise grinding of the lyophilized material aids in the homogeneity of reconstitution and protein stability. Previous methods involve crude grinding methods, including grinding or chopping of the material in a household blender. In the present invention, some embodiments employ a commercial grinding apparatus to machine the material to a homogenous particle size. In some embodiments, a pharmaceutical mill is employed. In other embodiments, the particle size is 1 millimeter or less in diameter.

It is also important to remove the static charge from the ground material to make it easier to work with. Accordingly, in some embodiments, the ground material has been deionized.

6. EXAMPLES

6.1 Example 1—Keratose Extraction Methods (Oxidative Extraction)

Untreated Chinese hair was used in the extraction method. The hair was end-cut to lengths of ¼, ½, ¾ and 1 inch segments and cleaned by washing in a warm water solution.

Step 1: The hair was added to a mixing tank. The tank was a 316L stainless steel vessel that contained a propeller for mechanical agitation (see FIG. 1). The oxidant was added to the vessel. The oxidant used was a 2% solution of paracetic acid (PAA) at a 25:1 weight-to-weight ratio. The mixture was mechanically mixed for a period of 12 hours at 37° C. The mechanical mixing resulted in complete oxidation of the hair shafts (see FIG. 2).

Step 2: The residual solution containing the oxidant was drained, neutralized and discarded.

Step 3: The oxidized hair was collected and rinsed with water until PAA test strips revealed no residual oxidant in the solution.

Step 4: A base was then added to the drained hair in a ratio of 25:1. In this Example, a 100 mM Tris base was used. The solution was mixed with mechanical agitation in the mixing tank for 2 hours at 37° C. FIGS. 3A and 3B show hair that has completed this extraction step.

Step 5: The solution containing base and extracted keratin proteins was then collected and stored in a separate container at 4° C. The remaining hair was retained by sieving through a steel mesh with a pore size of the mesh of 400 microns. The mechanical agitation employed in this step helped to remove any residual extracted solution from the remaining hair mass.

Step 6: Purified water was then added to the hair at a ratio of 25:1 and mixed for 2 hours at 37° C.

Step 7: The solution containing water and extracted keratin proteins was then collected and added to the solution from Step 5 in a separate container stored at 4° C. In order to get the maximum extraction yield, the hair was sieved through a steel mesh with a pore size of 400 microns The mechanical agitation employed ensures removal of any residual extracted solution from the remaining hair mass. FIG. 4 shows the hair shafts after the final water extraction.

Step 8: The combined mixture from Step 5 and Step 7 was then centrifuged at 20,000 rpm to remove any solids or beta-keratins. Centrifugation at speeds at or below 4,000 rpm does not fully remove residual solids, contributing to poor dialysis and final product.

Step 9: The centrifuged solution was filtered with a 20 micrometer pore size capsule filter.

Step 10: The solution from Step 9 was dialyzed against a 100 kDa molecular weight cut off dialysis membrane, made from regenerated cellulose, using standard tangential flow filtration. It can be beneficial to cool the solution to minimize heat from shear forces on pumps. It can also be beneficial to maintain trans-membrane pressures between 30-40 psi during the dialysis process. Lower pressures result in solutions that contain greater protein fragments and peptides, higher pressures result in protein complex degradation. The solution was dialyzed until the conductivity reached 0.6 mS using additions of purified water to replace permeate. The first complete solution wash was collected and stored in a storage tank at 4° C.

Step 11: The solution from Step 10 was then lyophilized into a keratin protein cake of alpha keratose. The lyophilization step helps maintain intact keratin proteins. The solution was bulk frozen to −40° C. quickly then had a vacuum applied until the containment vessel containing the protein reached 250 torr. Heat was then applied in a step-wise fashion to bring the material first to 0° C., then to 25° C., then to 37° C. while maintaining 250 torr. The temperature was maintained at 37° C. in order to prevent degradation during the drying process.

Step 12: The first wash solution from Step 10 (containing gamma-keratose) was dialyzed against a 5 kDa molecular weight cut off dialysis membrane made from regenerated cellulose, using standard tangential flow filtration methods. The solution was cooled to minimize the heat build-up from shear forces on the pumps. Also, the trans-membrane pressures were maintained between 50-70 psi during the dialysis process. Lower pressures result in solutions that contain greater protein fragments and peptides, higher pressures result in protein complex degradation. The solution was dialyzed until the conductivity reached 0.6 mS using additions of purified water to replace permeate.

Step 13: The solution from Step 12 was lyophilized into a keratin protein cake of gamma-keratose. The solution containing the gamma-keratose was bulk frozen at −40° C. quickly then the vacuum was applied until the containment vessel containing the protein reached 250 torr. Heat was then applied in a step-wise fashion to bring the material first to 0° C., then to 25° C., then to 37° C. while maintaining 250 torr. The mixture was maintained at 4° C. Elevated temperatures in the method were avoided in order to prevent degradation during the drying process.

Step 14: The keratin protein cakes from Step 11 and 13 were independently ground using a pharmaceutical mill with a mesh size of 1 millimeter. The ground protein was deionized to better allow further processing. The ground protein was then placed in sterile bags and is now ready for use in a variety of medical and research applications.

6.2 Example 2—Kerateine Extraction Methods (Reductive Extraction)

Kerateine extraction methods (reductive extraction).

Untreated Chinese hair was end-cut to lengths of ¼, ½, ¾ and 1 inch segments and washed in a warm water solution.

Step 1: The hair was added to a 316L stainless steel vessel that contained a propeller for mechanical agitation (see FIG. 1). The reductant was added to the vessel. The reductant was a 0.5M solution of a thioglycolic acid (TGA) at a ratio of 25:1. The mixture was mechanically mixed for a period of 15 hours at 37° C. The mechanical mixing can be beneficial to improve the extent to which reduction occurs in the hair shafts.

Step 2: The solution containing reductant and extracted keratin proteins was collected and stored in a separate container at 4° C. The remaining hair was retained by sieving through a steel mesh with a pore size of 400 microns. The mechanical agitation applied during the straining process helps to collect as much solution as possible from the hair mass.

Step 3: A base was then added to the drained hair in a ratio of 25:1. The base used here was a 100 mM Tris base solution. The solution was mixed with mechanical agitation in a mixing tank for 2 hours at 37° C.

Step 4: The solution containing base and extracted keratin proteins was collected and added to the solution from Step 2 and stored at 4° C. The remaining hair was retained by sieving through a steel mesh with a pore size of 400 microns. The mechanical agitation applied during the straining process helps to collect as much solution from the hair mass.

Step 5: Purified water was added to the hair at a ratio of 25:1 and mixed for 2 hours at 37° C.

Step 6: The solution containing water and extracted keratin proteins was collected and added to the solution from Step 4 and stored at 4° C. In order to maximize extraction yield, the hair was sieved through a steel mesh with a pore size of 400 microns. Mechanical agitation was applied during the straining process to strain as much solution as possible from the hair mass.

Step 7: A second reduction step was needed to fully extract the keratin proteins from the hair shaft. The reductant used was a 0.5M solution of a thioglycolic acid (TGA) at a ratio of 25:1. The mixture was mechanically mixed for a period of 15 hours at 37° C. Mechanical mixing was used to ensure complete reduction of the hair shafts.

Step 8: The solution containing reductant and extracted keratin proteins wascollected and stored in a separate vessel containing the solution from Step 6 and stored at 4° C. The remaining hair was retained by sieving through a steel mesh with a pore size of 400 microns. Mechanical agitation applied during the straining process helps to strain as much solution from the hair mass.

Step 9: A base was added to the drained hair in a ratio of 25:1. The base used was a 100 mM Tris base solution. The solution was mixed with mechanical agitation in a mixing tank for 2 hours at 37° C.

Step 10: The solution containing base and extracted keratin proteins was then collected and added to the solution from Step 8 and stored at 4° C. The remaining hair was retained by sieving through a steel mesh with a pore size of 400 microns. Mechanical agitation applied during the straining process helps to strain as much solution as possible from the hair mass.

Step 11: Purified water was then added to the hair at a ratio of 25:1 and mixed for 2 hours at 37° C.

Step 12: The solution containing water and extracted keratin proteins was collected and added to the solution from Step 10 stored at 4° C. In order to get the maximum extraction yield, the hair was sieved through a steel mesh of a pore size of 400 microns. Again, mechanical agitation applied during the straining process helps to strain as much solution as possible from the hair mass.

Step 13: The combined mixture from Steps 12, 10, 8, 6, 4, and 2 was centrifuged at 20,000 rpm to remove any solids or beta keratins. Centrifugation at speeds at or below 4,000 rpm does not fully remove residual solids, contributing to poor dialysis and final product.

Step 14: The centrifuged solution was filtered with a 20 micrometer pore size capsule filter.

Step 15: The solution from Step 14 was dialyzed against a 100 kDa molecular weight cut off regenerated cellulose dialysis membrane using standard tangential flow filtration methods. The solution was cooled to dissipate the heat from shear forces on pumps. Also, trans-membrane pressures were maintained between 30-40 psi during the dialysis process. The solution was dialyzed until the conductivity lowered from 24 mS to 0.6 mS using additions of purified water to replace permeate. This required about 5 complete volume changes (or washes) and left some residual TGA in the solution. The TGA can be completely removed by dialyzing until the conductivity reaches 0 mS or 12-20 volume changes. The first complete solution wash was collected and stored in a storage tank at 4° C.

Step 16: The solution from Step 15 was lyophilized into a keratin protein cake of alpha keratin. A lyophilization step was used to maintain intact keratin proteins. Generally, methods that are known in the art such as shell freezing followed by vacuum or bulk freezing and applying high heat tend to degrade the proteins. Here, the lyophilization step was to bulk freeze the solution to −40° C. quickly then apply a vacuum until the containment vessel containing the protein reached 250 torr. Heat was applied in a step-wise fashion to bring the material first to 0° C., then to 25° C., then to 37° C. while maintaining 250 torr. The temperature was not allowed to exceed 37° C. in order to prevent degradation during the drying process.

Step 17: The first wash solution from Step 15 (gamma kerateine) was dialyzed against a 5 kDa molecular weight cut off regenerated cellulose dialysis membrane using standard tangential flow filtration methods. Heat from shear forces on pumps was minimized by cooling the solution. Also, trans-membrane pressures between 50-70 psi were maintained during the dialysis process. Lower pressures result in solutions that contain greater protein fragments and peptides, higher pressures result in protein complex degradation. The solution was dialyzed until the conductivity reached 0.6 mS using additions of purified water to replace permeate.

Step 18: The solution from Step 17 was lyophilized into a keratin protein cake of gamma-kerateine. Here, lyophilization was accomplished by bulk freezing the solution to −40° C. quickly then applying a vacuum until the containment vessel containing the protein reached 250 torr. Heat was then applied in a step-wise fashion to bring the material first to 0° C., then to 25° C., then to 37° C. while maintaining 250 torr. The temperature was not allowed to exceed 37° C. in order to prevent degradation during the drying process.

Step 19: The keratin protein cakes from Step 18 and 16 were independently ground using a pharmaceutical mill with a mesh size of 1 millimeter. The ground protein was deionized to better allow further processing. The ground protein was then placed in sterile bags and is now ready for use in a variety of medical and research applications.

We claim:
1. A method for extracting keratin proteins comprising:
   a. Treating a keratin protein source with an oxidizing or reducing agent to solubilize keratin proteins;
   b. Separating the soluble proteins from the keratin protein source by high speed centrifugation to produce a clarified soluble keratin protein solution; and
   c. Dialyzing the clarified soluble keratin protein solution to obtain a soluble keratin protein solution which exhibits a conductivity of 0.6 mS or less,
   wherein said keratin protein is keratose.

2. The method of claim 1, wherein said high speed centrifugation is performed at 5,000 rpm or higher.

3. The method of claim 1, wherein said clarified soluble keratin protein solution comprises less than 5% beta-keratin.

4. The method of claim 1, wherein said method comprises dialyzing the clarified soluble keratin protein solution against a 5 kDa molecular weight membrane.

5. The method of claim 1, wherein said dialysis is performed at a pressure from about 10 psi to about 70 psi.

6. The method of claim 5, wherein the dialysis permeate comprises gamma-keratose.

7. The method of claim 1, wherein the soluble keratin protein solution is lyophilized into a keratin protein cake.

8. The method of claim 1, wherein said soluble keratin protein solution comprising at least 90% or more keratose.

9. The method of claim 8, wherein said soluble keratin protein solution comprises at least 90% or more alpha-keratose.

10. A method for extracting keratin proteins comprising:
    a. Treating a keratin protein source with an oxidizing or reducing agent to solubilize keratin proteins;
    b. Separating the soluble proteins from the keratin protein source by high speed centrifugation to produce a clarified soluble keratin protein solution; and
    c. Dialyzing the clarified soluble keratin protein solution to obtain a soluble keratin protein solution which exhibits a conductivity of 0.6 mS or less,
    wherein said soluble keratin protein solution comprising at least 90% or more keratose.

11. A method for extracting keratin proteins comprising:
    a. Treating a keratin protein source with an oxidizing or reducing agent to solubilize keratin proteins;
    b. Separating the soluble proteins from the keratin protein source by high speed centrifugation to produce a clarified soluble keratin protein solution; and
    c. Dialyzing the clarified soluble keratin protein solution to obtain a soluble keratin protein solution which exhibits a conductivity of 0.6 mS or less,
    wherein said dialysis is performed at a pressure from about 10 psi to about 70 psi.

12. The method of claim 11, wherein said keratin protein is kerateine.

\* \* \* \* \*